(12) United States Patent
Swenson

(10) Patent No.: US 8,231,583 B2
(45) Date of Patent: Jul. 31, 2012

(54) SAFETY NEEDLE ASSEMBLY WITH PASSIVE PIVOTING SHIELD

(75) Inventor: Kirk D. Swenson, North Caldwell, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1954 days.

(21) Appl. No.: 10/309,904

(22) Filed: Dec. 4, 2002

(65) Prior Publication Data

US 2004/0111068 A1  Jun. 10, 2004

(51) Int. Cl.
*A61M 5/32* (2006.01)
(52) U.S. Cl. .................. 604/198; 604/192; 604/110
(58) Field of Classification Search .......... 604/187, 604/192, 198, 263, 110; 128/919; 600/576, 600/577
See application file for complete search history.

(56) References Cited

U.S. PATENT DOCUMENTS

| | | | | |
|---|---|---|---|---|
| 4,887,998 | A * | 12/1989 | Martin et al. | 604/110 |
| 4,946,446 | A | 8/1990 | Vadher | |
| 5,188,611 | A | 2/1993 | Orgain | |
| 5,295,975 | A | 3/1994 | Lockwood, Jr. | |
| 5,312,369 | A | 5/1994 | Arcusin et al. | |
| 5,445,619 | A * | 8/1995 | Burns | 604/192 |
| 5,492,536 | A * | 2/1996 | Mascia | 604/197 |
| 5,718,239 | A * | 2/1998 | Newby et al. | 600/576 |
| 5,893,845 | A | 4/1999 | Newby et al. | |
| 6,298,541 | B1 * | 10/2001 | Newby et al. | 29/458 |
| 6,616,637 | B2 * | 9/2003 | Alexander et al. | 604/192 |
| 7,361,159 | B2 * | 4/2008 | Fiser et al. | 604/192 |
| 2003/0181868 | A1 | 9/2003 | Swenson et al. | |

FOREIGN PATENT DOCUMENTS

| | | |
|---|---|---|
| EP | 680767 | 11/1995 |
| FR | 2 618 585 | 2/1989 |
| GB | 2 202 747 | 10/1988 |

* cited by examiner

*Primary Examiner* — Jackie Ho
*Assistant Examiner* — Laura Schell
(74) *Attorney, Agent, or Firm* — The Webb Law Firm

(57) ABSTRACT

A blood collection assembly includes a needle cannula, a hub mounted on the needle cannula, and a spring biased pivoting shield pivotably mounted to the hub and moveable about a pivot axis between a retracted position and a shielded position encompassing a distal end of the needle cannula. A needle holder is mated at a first end with the hub, and is adapted for receiving a blood collection container such as an evacuated tube through the opposing end. A retaining member is attached to the pivoting shield and is releasably engageable with the hub to maintain the pivoting shield in the retracted position against the spring bias. Insertion of a blood collection tube into the needle holder causes the retaining member to release from engagement with the hub, thereby causing the pivoting shield to move toward the shielded position due to the spring bias.

25 Claims, 20 Drawing Sheets

SAFETY NEEDLE ASSEMBLY WITH PASSIVE PIVOTING SHIELD

BACKGROUND OF THE INVENTION

1. Field of the Invention

The present invention relates to a safety needle assembly with a pivoting shield that is activated during a standard sequence of operation of a medical procedure and, more particularly, relates to a needle and hub assembly having a pivoting shield that is passively pivoted to a shielding position when a sampling tube is inserted within a needle holder.

2. Description of Related Art

An evacuated collection tube, needle cannula (generally a double ended needle cannula) and needle holder are commonly used by a doctor, phlebotomist, or nurse to draw a sample of body fluid from a patient in a hospital or doctor's office for diagnostic testing. During the use of such a collection needle assembly, the distal end of the needle cannula in the needle holder is inserted in a vein of the patient. The evacuated collection tube is then inserted into the proximal end of the needle holder until a needle (the proximal end of a double ended needle cannula) within the needle holder pierces a closure on the end of the tube. The vacuum in the tube then draws a body fluid sample from the patient through the needle cannula and into the tube. After the collection process is complete the needle cannula is removed from the vein and disposed of.

Because of the great concern that users of such needles may be contaminated with the blood of a patient by accidental sticks from the contaminated needle, it is preferable to cover the contaminated needle as soon as it is removed from the vein. For this reason, many developments have been made to provide means for covering the contaminated needle, once it is removed from the patient. These devices usually involve some sort of shield arrangement that moves in place over the contaminated needle once it has been removed from the patient. However, these shield arrangements typically require the use of one or two hands to perform the operation of moving the shield over the contaminated needle, which is a hindrance to the user.

U.S. Pat. Nos. 5,718,239 and 5,893,845 provide safety needle assemblies incorporating a telescoping shield that extends over the distal end of the needle cannula when released by an actuator that is triggered during a standard sequence of operation of a medical procedure. In particular, when the closure or stopper on the collection tube is pierced by the proximal end of the needle cannula, an actuator is triggered to cause the telescoping shield to extend to contact the skin of a patient. Then, when the needle end of the cannula is removed from the patient the telescoping shield continues to extend to a fully extended and locked position over the distal end of the needle cannula, thereby rendering the needle assembly safe and preventing needle stick injuries. While such assemblies provide effective needle shielding techniques, they involve complex mechanisms for activation, and deployment of the telescoping shield may disrupt the patient.

A number of devices incorporate a pivoting shield assembly in which the shield can be pivoted away from the needle during use and pivoted about the needle after use for protection from the used needle. U.S. Pat. No. 5,188,611 discloses a reusable safety needle arrangement having a collar for engaging a needle and a slotted longitudinal shield which is attached to the collar at a hinge for pivoting over the needle. The arrangement includes a locking mechanism for locking the shield over the needle, which a locking mechanism is provided through a set of flanges on the shield which grip a set of complementary catches on the collar. U.S. Pat. No. 6,298,541 discloses a safety shield assembly for a double-ended needle for blood collection procedures with a pivoting shield attached to the needle hub through a collar. The hub includes threads for engaging a conventional needle holder such as that used with the VACUTAINER™ brand of blood collection assemblies sold by Becton, Dickinson and Company. While such shielding assemblies are effective, they require manual operation by the user in order to achieve effective shielding of the needle.

There is a need in the art for a safety assembly, which is automatically activated during the normal procedure used during blood collection and which does not involve a complex activation mechanism.

SUMMARY OF THE INVENTION

The present invention is directed to a shieldable needle assembly including a needle cannula having a proximal end and a distal end, with a hub mounted to the needle cannula at a location spaced from the distal end. A shield is pivotably mounted to the hub and is moveable about a pivot axis between a retracted position and a shielded position encompassing the distal end of the needle cannula. A biasing member, such as a spring, biases the pivoting shield towards the shielded position, and a lock releasably maintains the pivoting shield in the retracted position. The needle assembly further includes an actuator for releasing the lock. The actuator is activated to release the lock by pressure applied during a standard sequence of operation of a medical procedure, such as insertion of a blood collection tube into a needle holder, with the pivoting shield moving toward the shielded position upon activation of the actuator to release the lock.

The present invention is further directed to a blood collection assembly including a needle assembly having a needle cannula, a hub mounted on the needle cannula, and a spring biased pivoting shield pivotably mounted to the hub and moveable about a pivot axis between a retracted position and a shielded position encompassing a distal end of the needle cannula. A needle holder is with the hub of the needle assembly, and is adapted for receiving a blood collection container such as an evacuated tube. A retaining member is attached to the pivoting shield and is releasably engageable with the hub to maintain the pivoting shield in the retracted position against the spring bias. Insertion of a blood collection tube into the needle holder causes the retaining member to release from engagement with the hub, thereby causing the pivoting shield to move toward the shielded position due to the spring bias.

Desirably, the pivoting shield includes a retaining arm for engagement with the hub to form a lock for maintaining the pivoting shield in the retracted position against the spring bias. Further, one of the hub and the retaining arm may include a locking recess and the other of the hub and the retaining arm may include a locking lug, with the locking lug being engageable with the locking recess to form a lock. An actuator or actuating arm desirably extends from the hub and within the needle holder, and is capable of disengaging the locking lug from the locking recess to release the lock upon insertion of a blood tube within the needle holder through axial movement of the actuating arm. The actuating arm and the locking lug may include corresponding camming surfaces for causing the locking lug to move transversely with respect to the actuating arm upon axial movement of the actuating arm. The hub may also include a second locking recess for engagement with the retaining arm to secure the pivoting shield in the shielded position.

The biasing force of the spring is less than the force required to cause the retaining member to release from engagement with the hub. As such, the retaining member maintains the shield in the retracted position against the bias until release of the locking engagement between the retaining member and the hub.

The present invention further provides a method of shielding a needle. A needle holder is provided and is mated with a needle assembly which includes a hub mounted to a needle cannula with a spring biased pivoting shield mounted on the hub. The pivoting shield includes a retaining member engaging the hub to releasably maintain the pivoting shield against the spring bias to prevent the pivoting shield from moving to a shielded position encompassing the needle cannula. The method further includes inserting a blood collection tube into the needle holder to cause the retaining member to disengage from the hub, thereby causing the pivoting shield to be biased toward the shielded position. Desirably, an actuator extends between the needle holder and the needle assembly, such that inserting a blood collection tube into the needle holder causes axial movement of the actuator which causes the retaining member to disengage from the hub, thereby causing the pivoting shield to be biased toward the shielded position. The method may further include the step of locking the pivoting shield in the shielded position.

DESCRIPTION OF THE PREFERRED EMBODIMENTS

Figure 1:
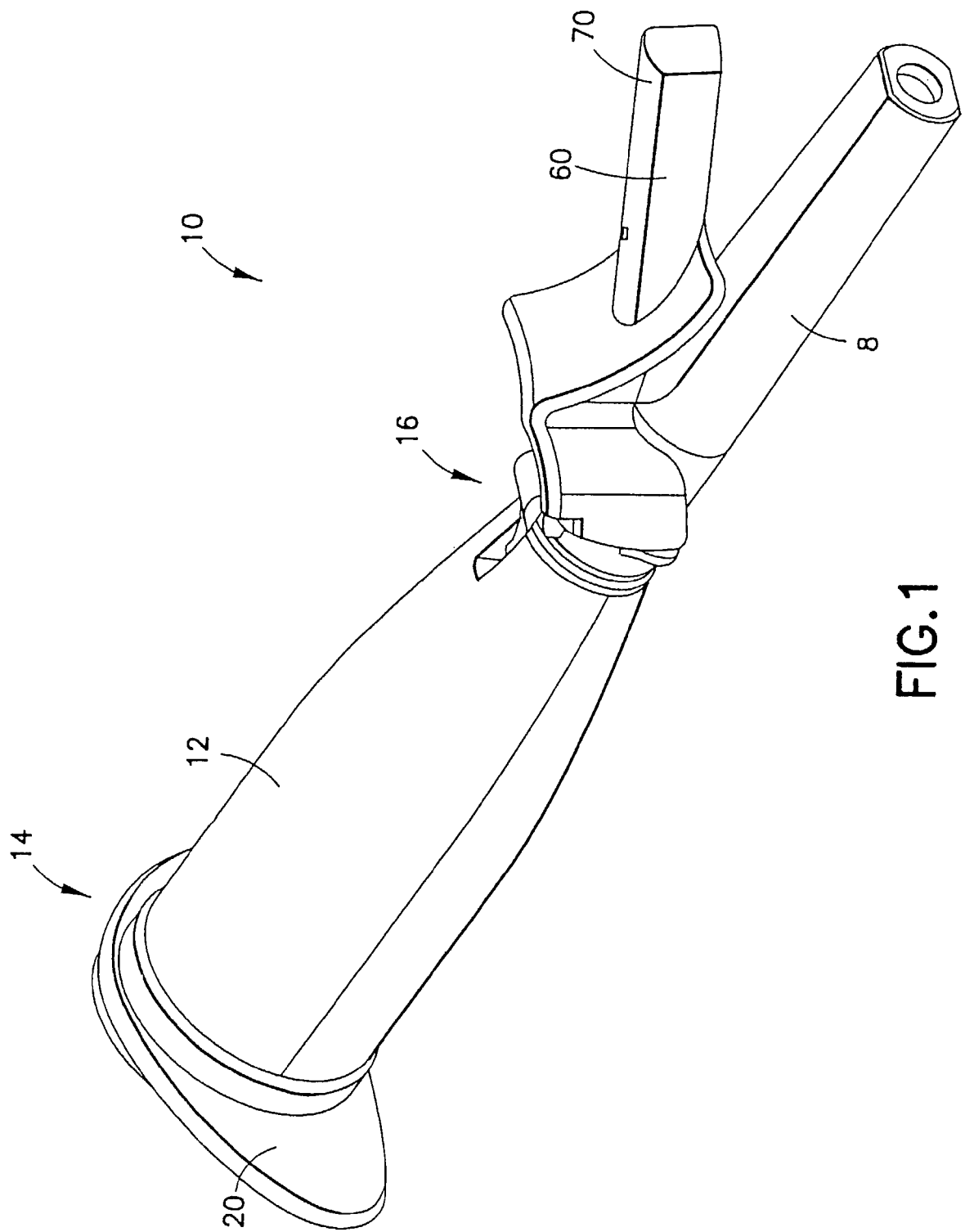
FIG. 1 is a perspective view of a blood collection assembly shown in a packaging state in accordance with one embodiment of the present invention.
Figure 2:
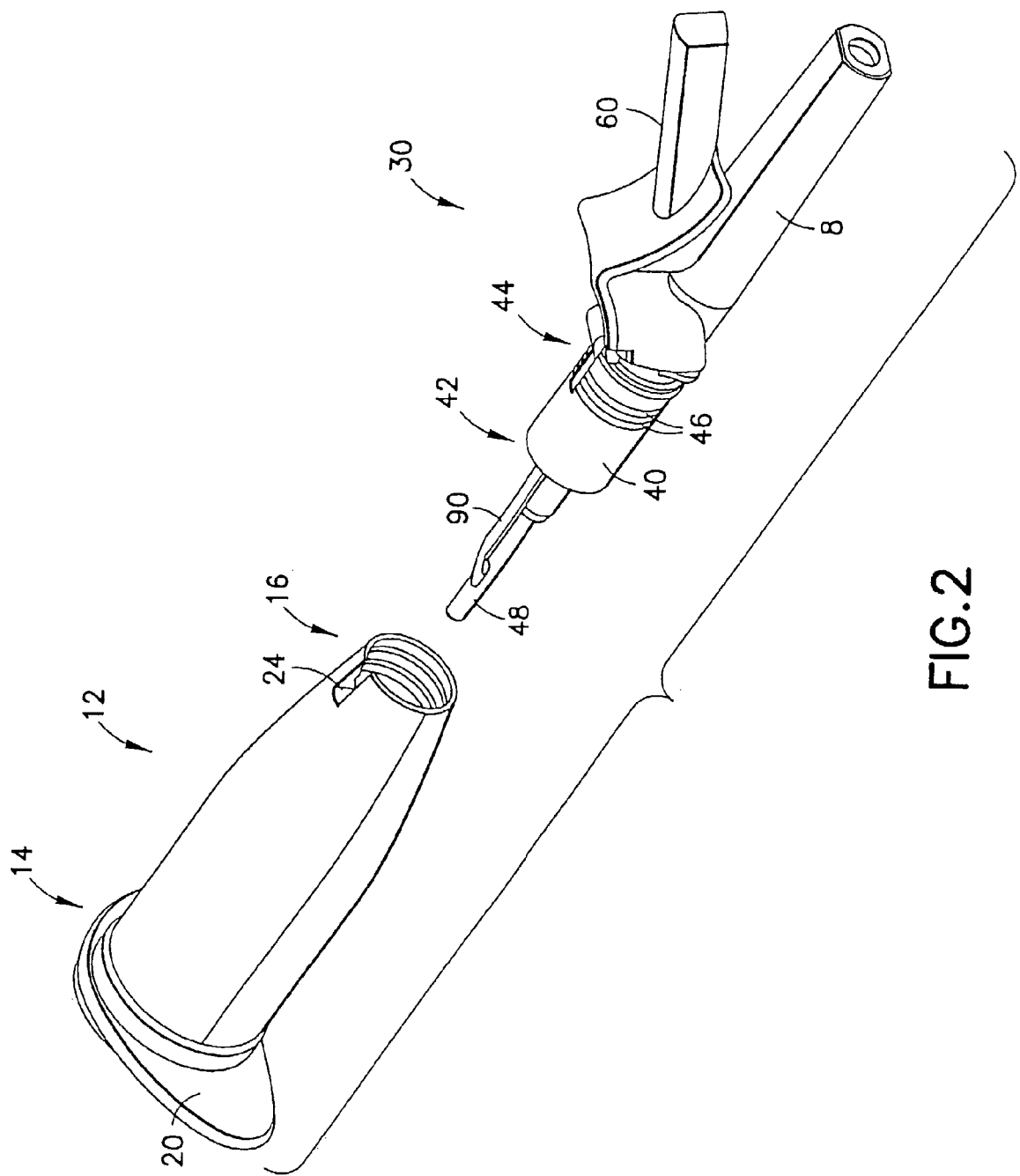
FIG. 2 is a perspective view of the blood collection assembly of FIG. 1 showing the needle assembly separated from the needle holder.
Figure 3:
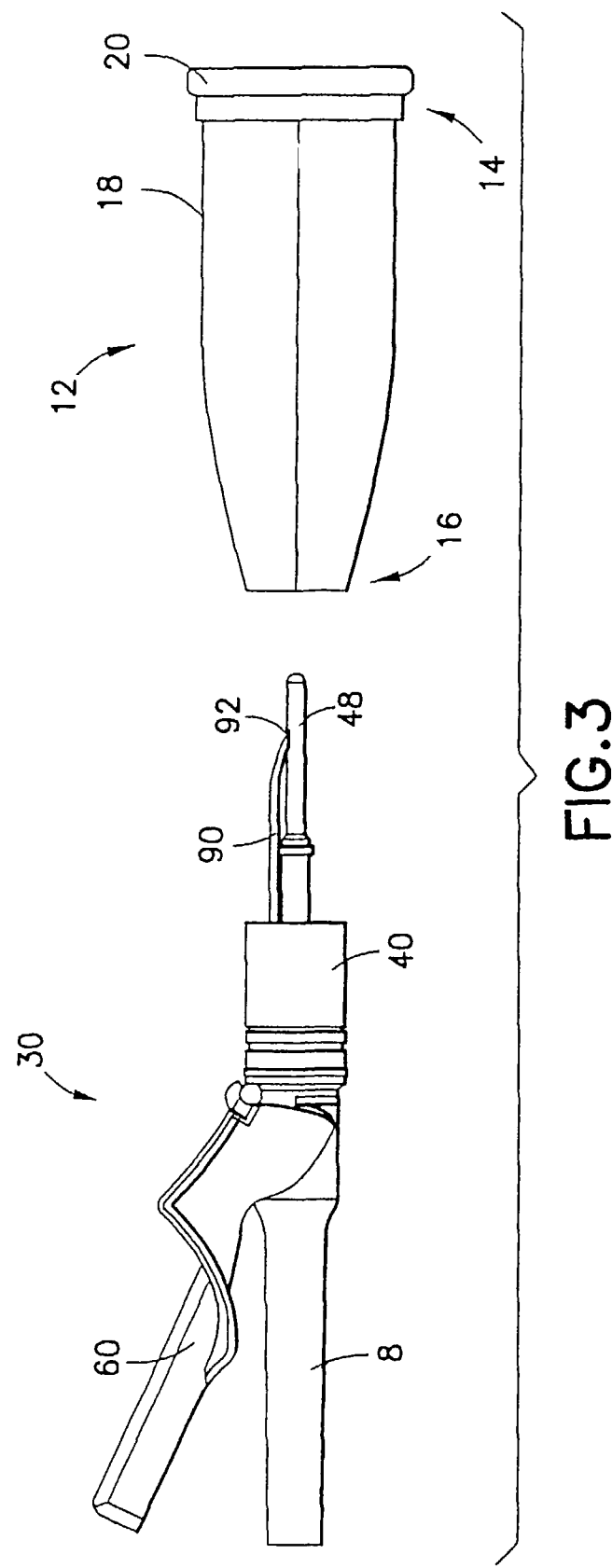
FIG. 3 is a side elevation view of the blood collection assembly as shown in FIG. 2 showing the needle assembly separated from the needle holder.

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

It is noted that the term "distal" as used herein refers to the end of the assembly that punctures the patient's skin, while the term "proximal" as used herein refers to the opposing end of the assembly that punctures a collection container.

Referring to the drawings in which like reference characters refer to like parts throughout the several views thereof, FIGS. 1-7 illustrate a blood collection assembly 10 including a needle holder 12 and a shieldable needle assembly 30 in accordance with the present invention. Generally speaking, the safety needle assembly of the present invention is in the form of a modified double-ended needle assembly for mating with a needle holder capable of accommodating a collection tube for sampling procedures. The present invention is set forth in terms of a needle assembly, as well as a blood collection assembly including a needle assembly mated with a needle holder.

Figure 14:
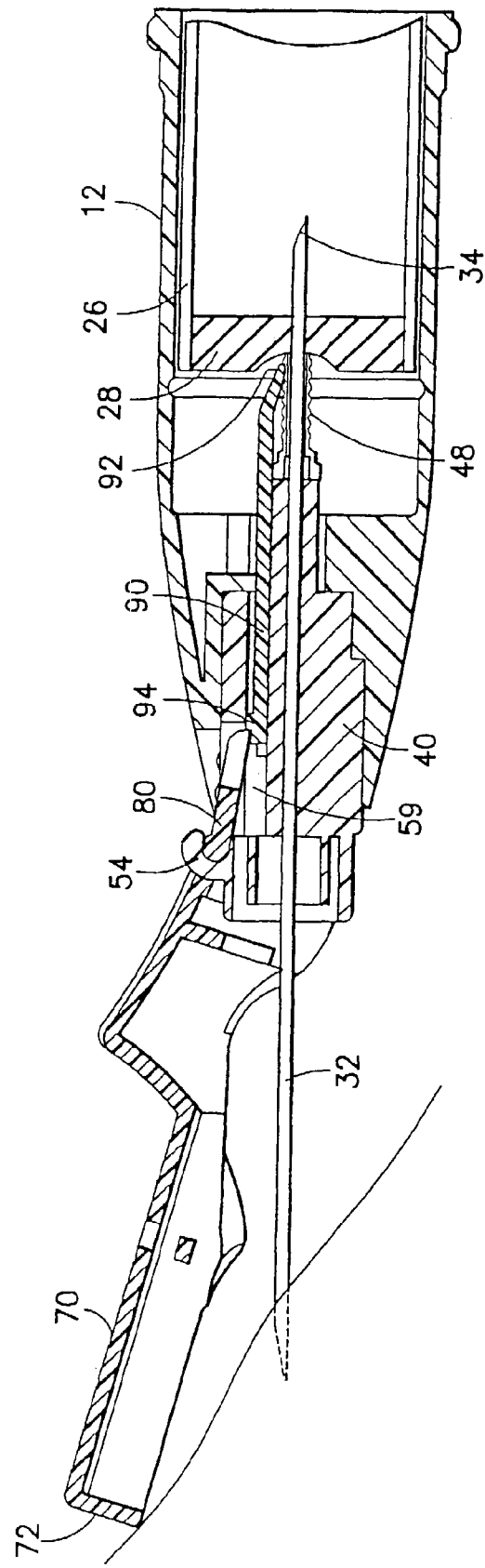
FIG. 14 is a side cross-sectional view of the blood collection assembly of the present invention in use during insertion of a blood collection tube within the needle holder.

Needle holder 12 includes a generally tubular body extending between a proximal end 14 and a distal end 16, and defined by tubular wall 18. Proximal end 14 of needle holder 12 is widely open and is adapted to receive a blood collection tube 26 as shown in FIG. 14. However, proximal end 14 of needle holder 12 may have a removable seal or cap (not shown) for maintaining sterility during storage. Proximal end 14 of needle holder 12 also includes a radially aligned flange 20 to facilitate manipulation of needle holder 12 during use. Flange 20 is desirably non-circular to prevent needle holder 12 from rolling. Flange 20 desirably includes a linear edge extending along a bottom surface of needle holder 12 to provide a clear indication of the top and bottom sides of needle holder 12.

Blood collection assembly 10 further includes needle assembly 30. Distal end 16 of needle holder 12 is adapted for mating with needle assembly 30. As such, needle holder 12 may include structure for mounting needle assembly 30 thereon. For example, distal end 16 of needle holder 12 may be formed with non-threaded mounting means, such that needle holder 12 is substantially fixed to needle assembly 30 after assembly. The non-threaded mounting means may comprise a combination of external rings, such as ribs 46, and keyways to secure needle assembly 30 to needle holder 12 axially and circumferentially. It is preferred that needle assembly 30 is mounted to needle holder 12 by the manufacturer to provide blood collection assembly 10 as a pre-assembled unit which is ready for fast and convenient use. Such a pre-assembled blood collection assembly 10 ensures that the proximal point of the needle is enclosed within needle holder 12 before, during, and after blood collection. Alternately, needle holder 12 and needle assembly 30 may be provided as distinct and separate components which are mated prior to use. As such, needle holder 12 and needle assembly 30 may include structure for easily mating therebetween, such as by providing the distal end 16 of the needle holder 12 with an internal array of threads that are engageable with corresponding external threads on the needle assembly 30. Alternatively, other means for mating engagement are also contemplated, such as a snap-fit connection, a releasable connection, and the like.

Needle assembly 30 includes a hollow needle cannula 32 having a proximal or rearward non-patient end 34 and a distal or forward intravenous end 36, with an internal lumen or passageway 38 extending therethrough. Distal end 36 of needle cannula 32 is beveled to define a sharp puncture tip for insertion into a patient's blood vessel, such as a vein, and is therefore designed to provide ease of insertion and minimal discomfort during venipuncture. Proximal end 34 of needle cannula 32 includes a sharp puncture tip typically provided for puncturing a stopper or septum of a collection tube during a blood collection procedure.

Needle cannula 32 may be supported by hub 40. Hub 40 includes a proximal end 42 and a distal end 44, with an internal passageway extending therethrough for accommodating needle cannula 32. Proximal end 34 of needle cannula 32 extends from proximal end 42, and distal end 36 of needle cannula 32 extends from distal end 44. It is contemplated that the proximal end 34 and the distal end 36 of needle cannula 32 may be provided as distinct and separate members joined through hub 40, so long as fluid flow is established between the two ends.

An elastomeric sleeve or sheath 48 may be provided about the proximal end 34 of needle cannula 32, extending from proximal end 42 of hub 40 and encompassing the proximal end 34 and the non-patient puncture tip of needle cannula 32.

Hub 40 may also include structure for maintaining a packaging cover, such as packaging cover 8, for protection of the distal end 36 of needle cannula 32 until use. For example, distal end 44 of hub 40 may include an outer annular skirt 50 and an inner annular skirt 52. As such, an end of packaging cover 8 can be removably mated with distal end 44 of hub 40 within the annular space between outer annular skirt 50 and inner annular skirt 52 in a frictional manner.

Blood collection assembly 10 further includes a shield 60 in pivotal engagement with needle cannula 32. Shield 60 includes a proximal end 62 and a distal end 64. Shield 60 includes a slot or longitudinal opening 66 formed by parallel sidewalls 68 that extend downwardly from top section 70 and run substantially opposite of one another in parallel along the length of slot 66 toward forward end wall 72.

Desirably, shield 60 is connected to needle assembly 30 through interengaging structure for providing pivotal attachment of shield 60 thereto. For example, hub 40 may include a hook member 54 extending from an outer surface thereof for pivotal engagement with a hanger bar 76 at proximal end 62 of shield 60, providing a pivot hinge for pivoting of shield 60 with respect to hub 40 and needle cannula 32 about a pivot axis.

Figure 7:
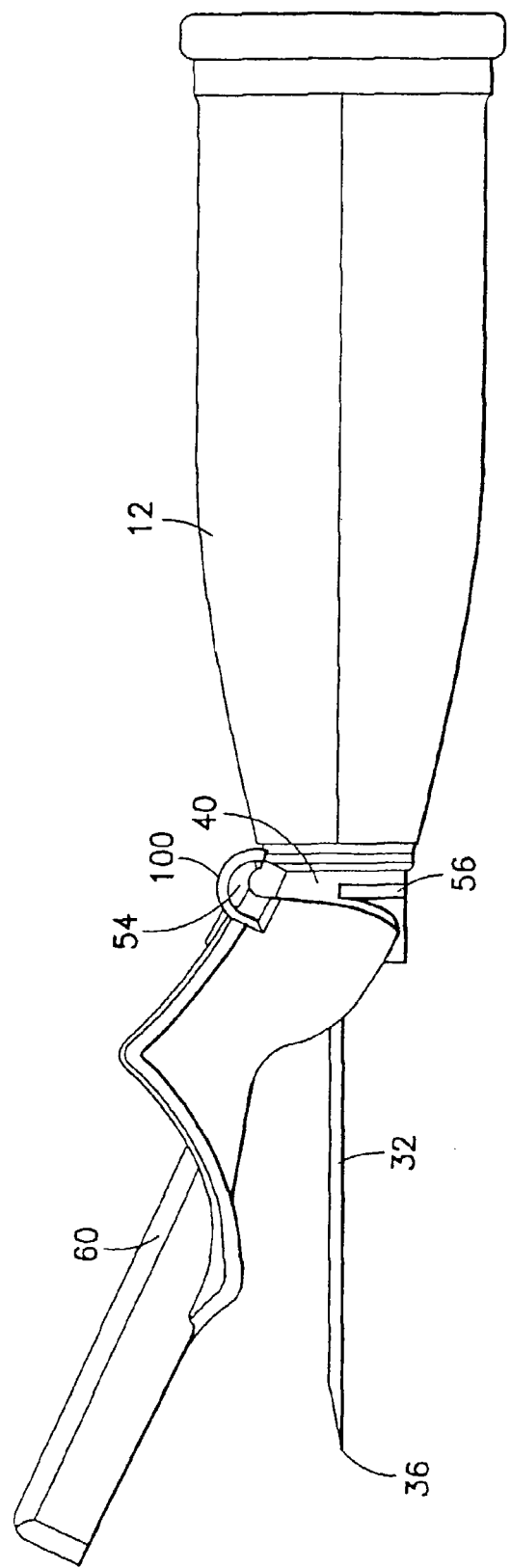
FIG. 7 is a side elevation view of the blood collection assembly of FIG. 6.
Figure 8:
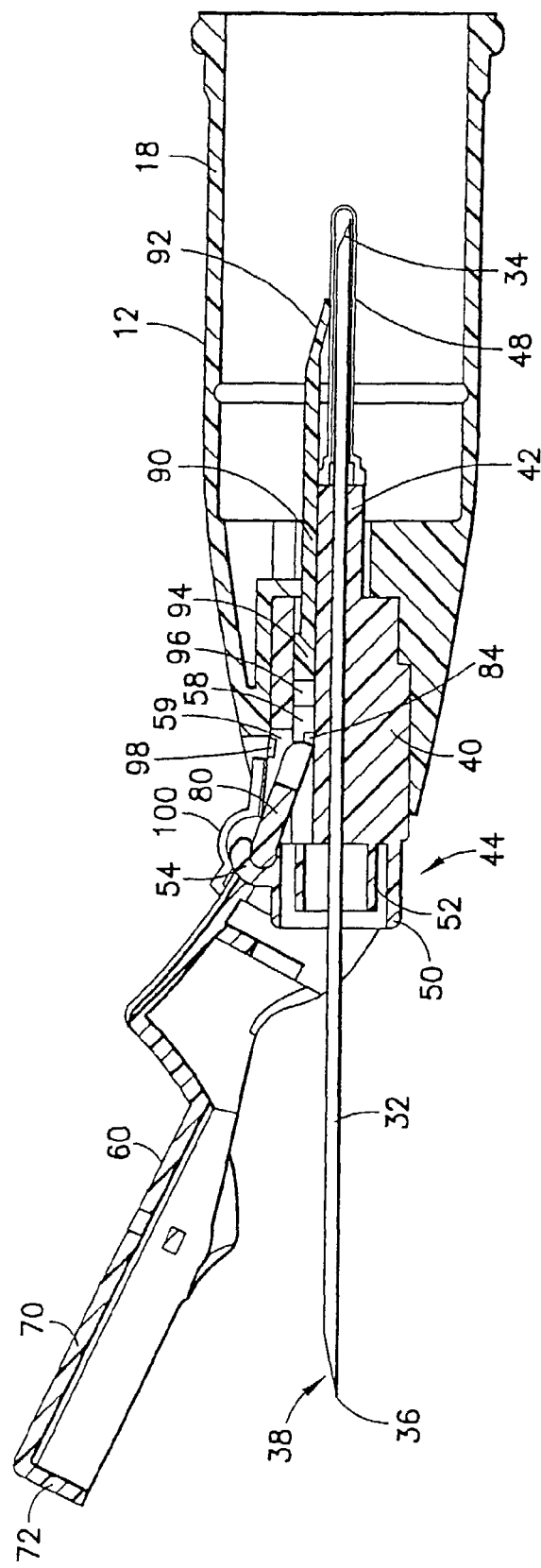
FIG. 8 is a side cross-sectional view of the blood collection assembly of FIG. 7.
Figure 9:
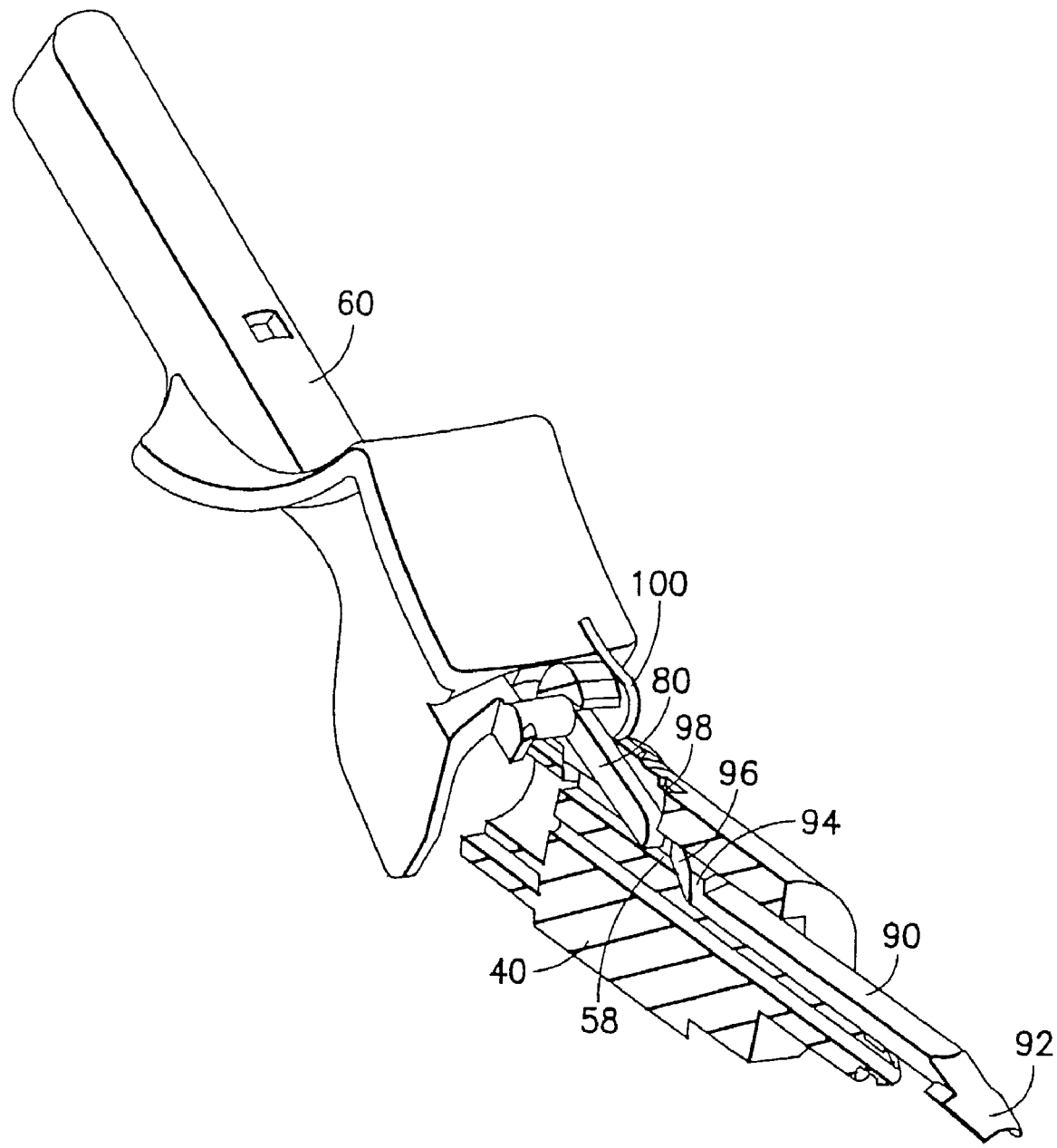
FIG. 9 is a rear perspective partial sectional view of the needle assembly of the present invention shown with the shield in the retracted position.
Figure 10:
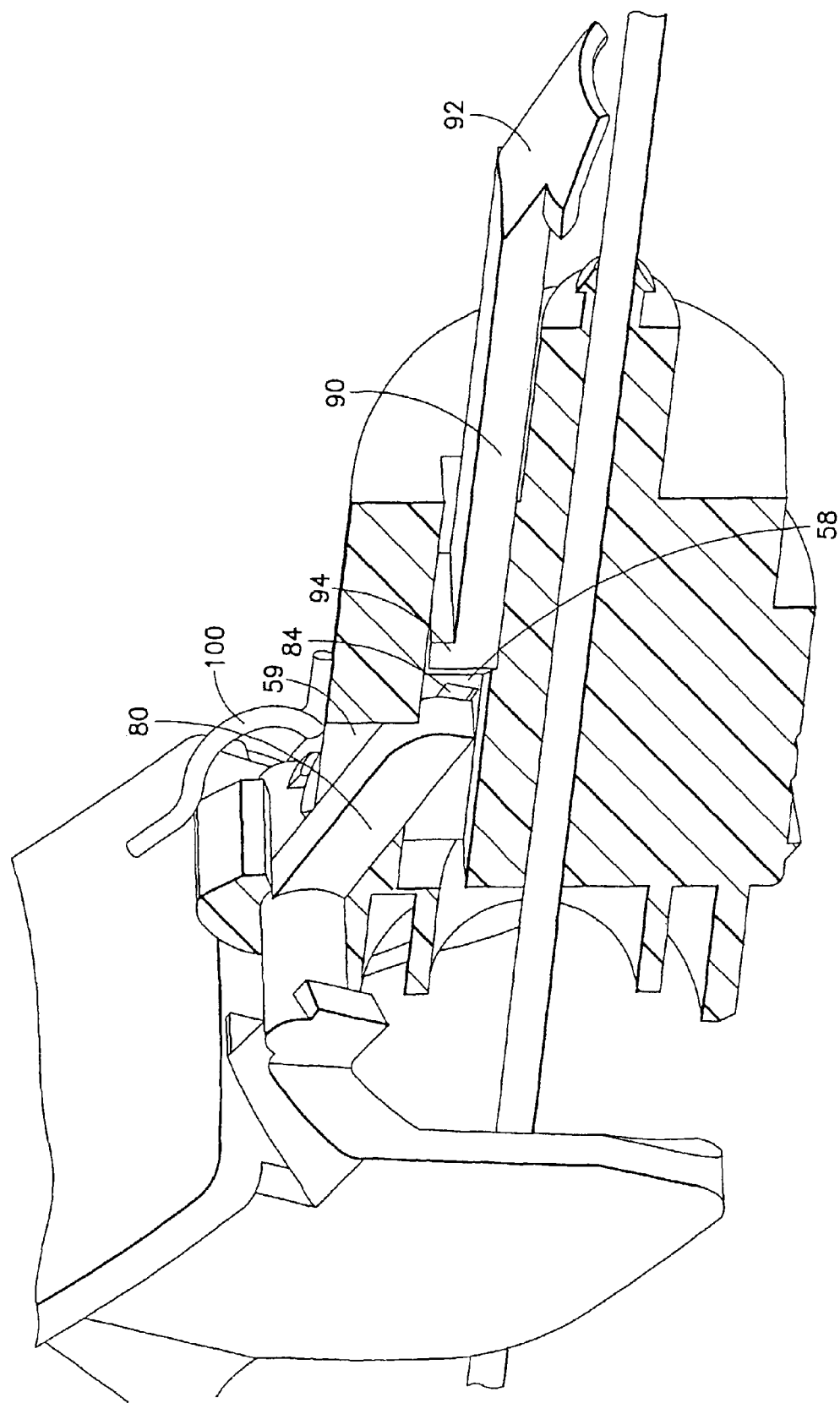
FIG. 10 is an enlarged view of a portion of FIG. 9 showing the engagement between the actuator and the retaining arm with the shield in the retracted position.
Figure 11:
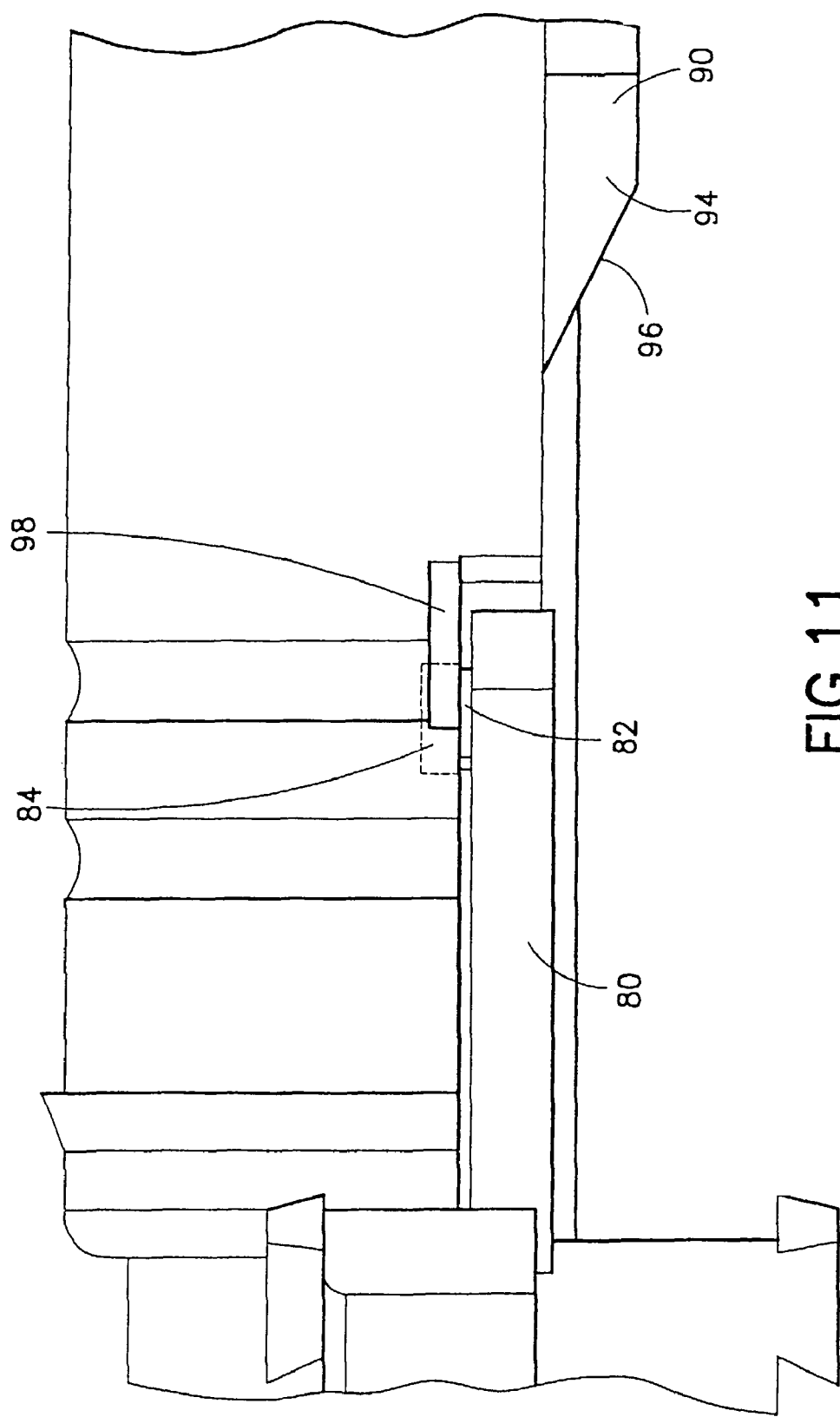
FIG. 11 is an enlarged top elevation view of a portion of FIG. 9 showing the engagement between the actuator and the retaining arm with the shield in the retracted position.
Figure 12:
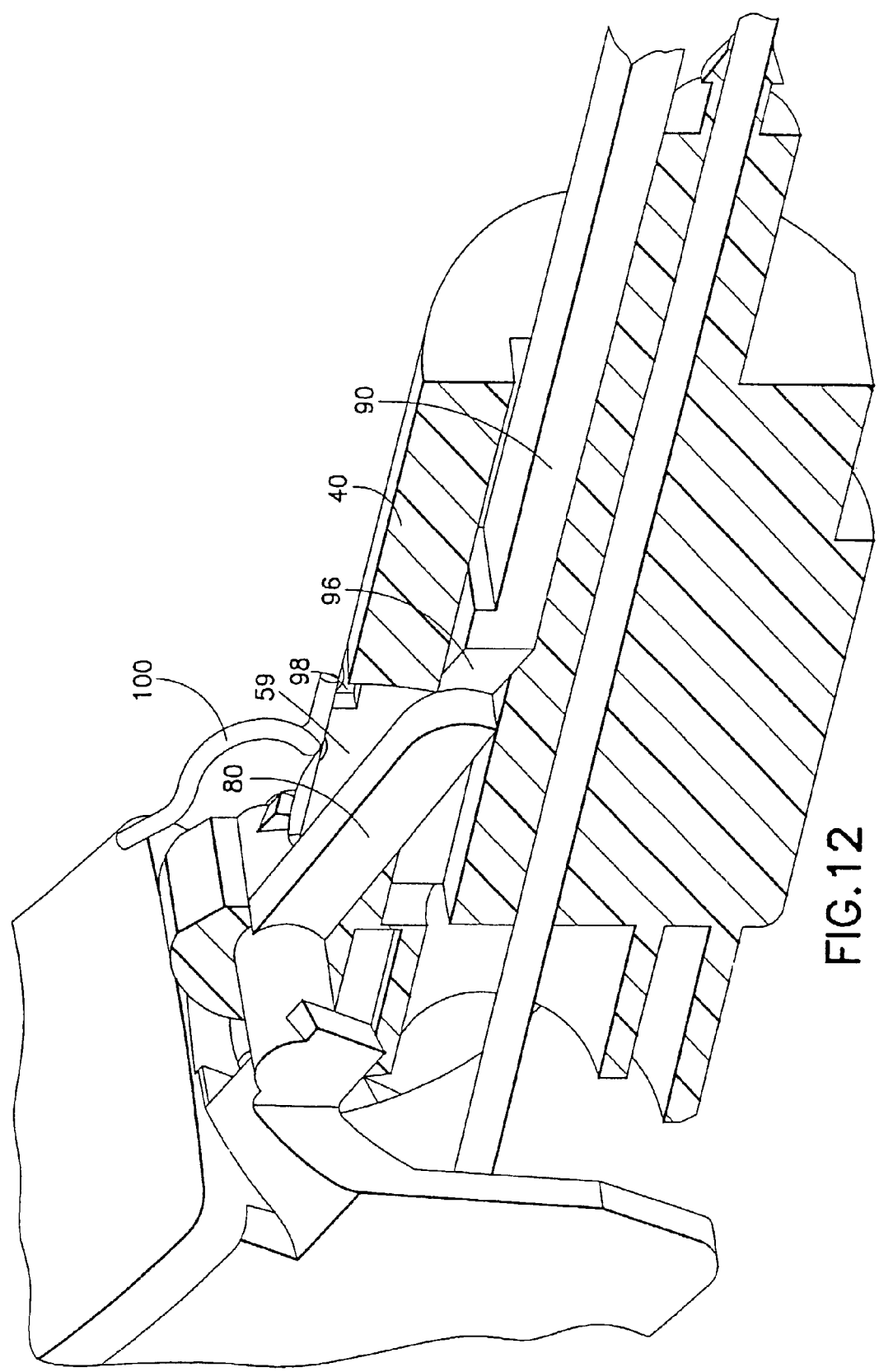
FIG. 12 is an enlarged view showing the engagement between the actuator and the retaining arm upon initial release of the shield from the retracted position.
Figure 13:
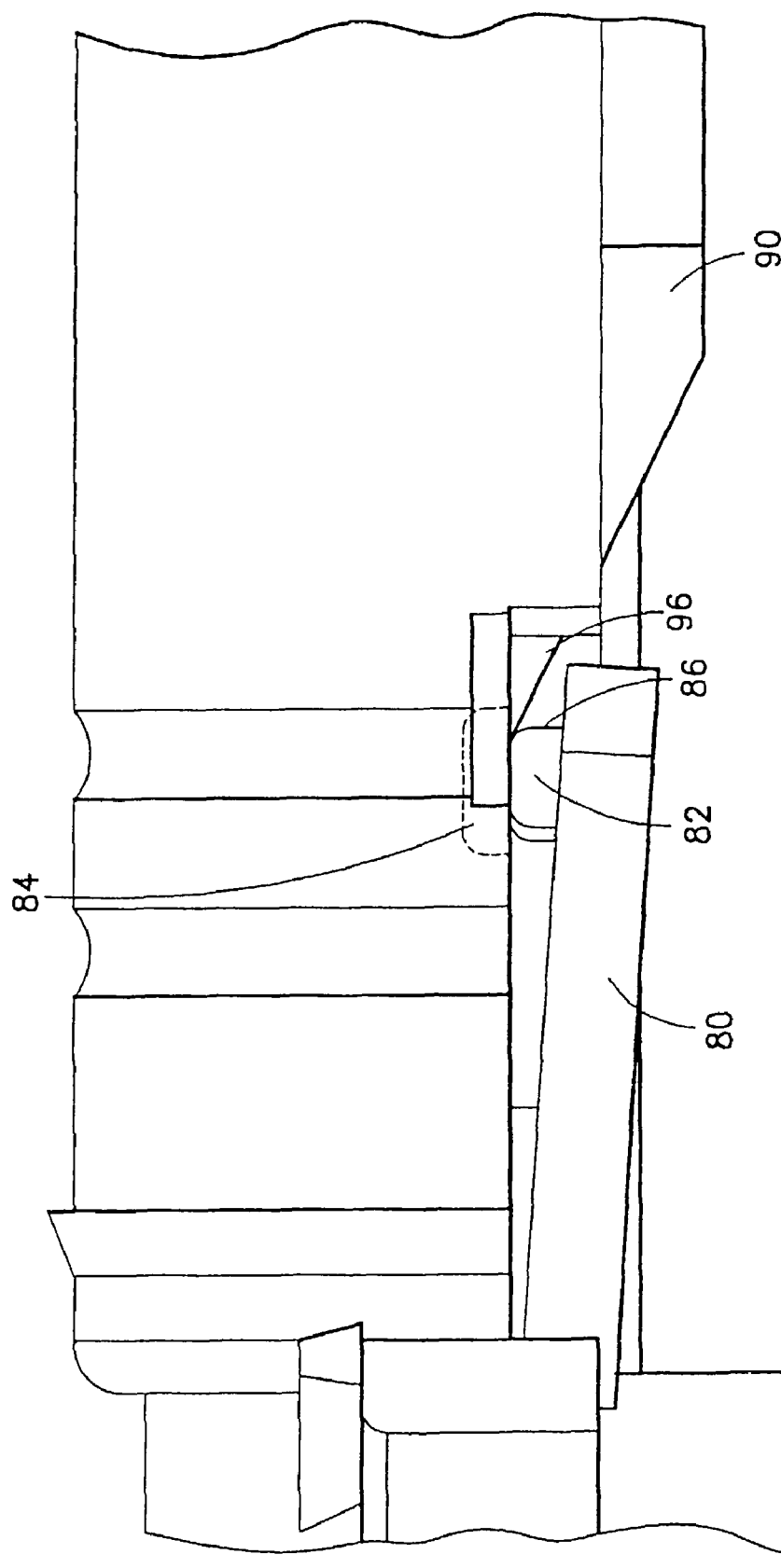
FIG. 13 is an enlarged top elevation view showing the engagement between the actuator and the retaining arm upon initial release of the shield from the retracted position.
Figure 19:
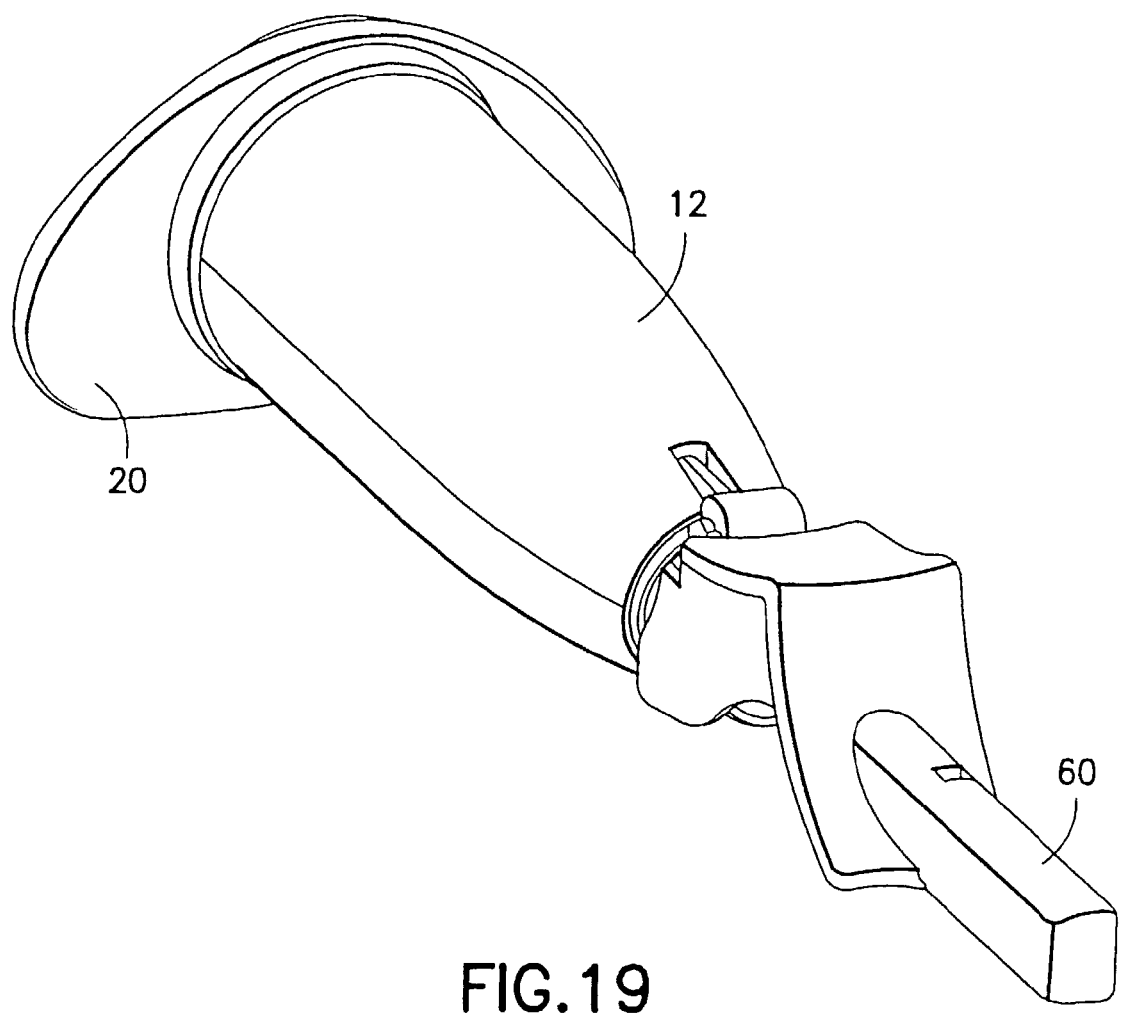
FIG. 19 is a perspective view of the blood collection assembly of the present invention in the fully shielded position.
Figure 20:
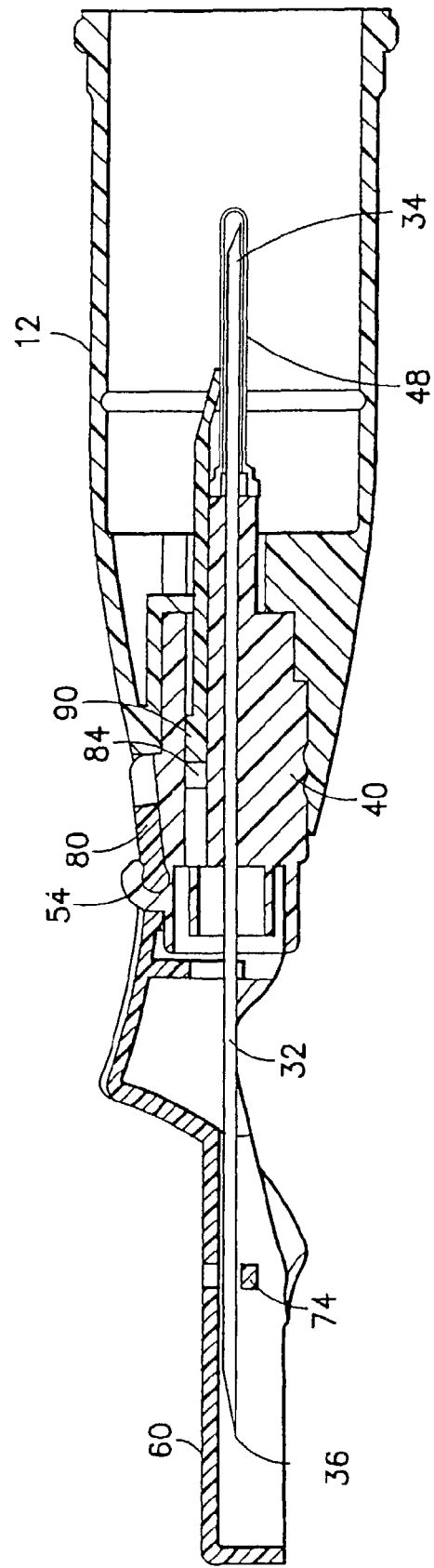
FIG. 20 is a side cross-sectional view of the blood collection assembly of FIG. 19 in the fully shielded position.

Hanger bar 76 is provided for pivotal engagement with hook member 54 of hub 40. Accordingly, the cooperating surfaces of hanger bar 76 and hook member 54 are designed so as to permit rotational or pivotal movement of shield 60 with respect to hub 40. Such engagement between hanger bar 76 and hook member 54 provides for pivotal movement of shield 60 between a retracted position as shown in FIGS. 7-8, with shield 60 pivotally spaced from distal end 36 of needle cannula 32, and a shielded position as shown in FIGS. 19-20, with shield 60 encompassing dital end 36 of needle cannula 32.

Figure 4:
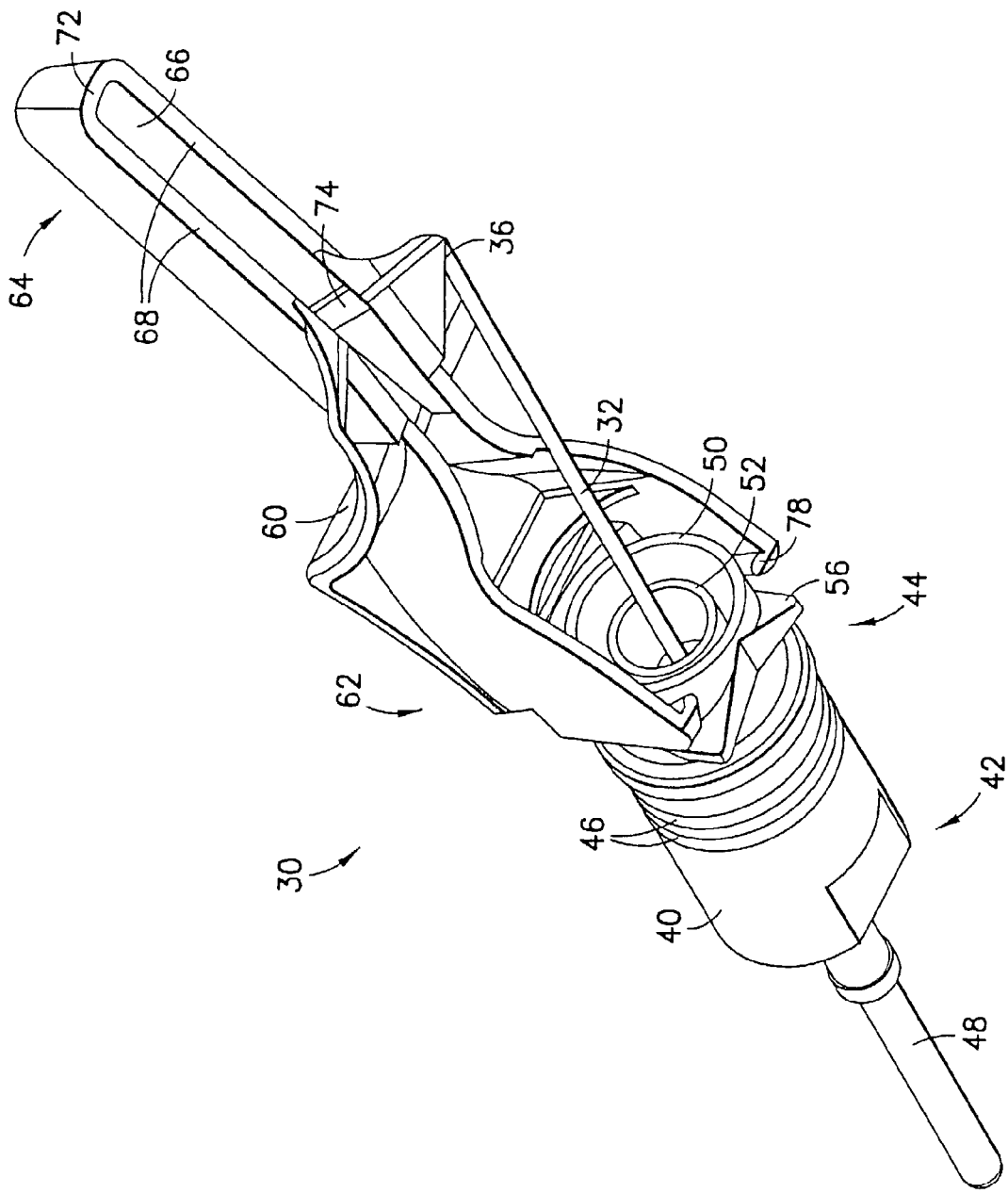
FIG. 4 is a bottom perspective view of the needle assembly of the present invention with the packaging cover removed.
Figure 5:
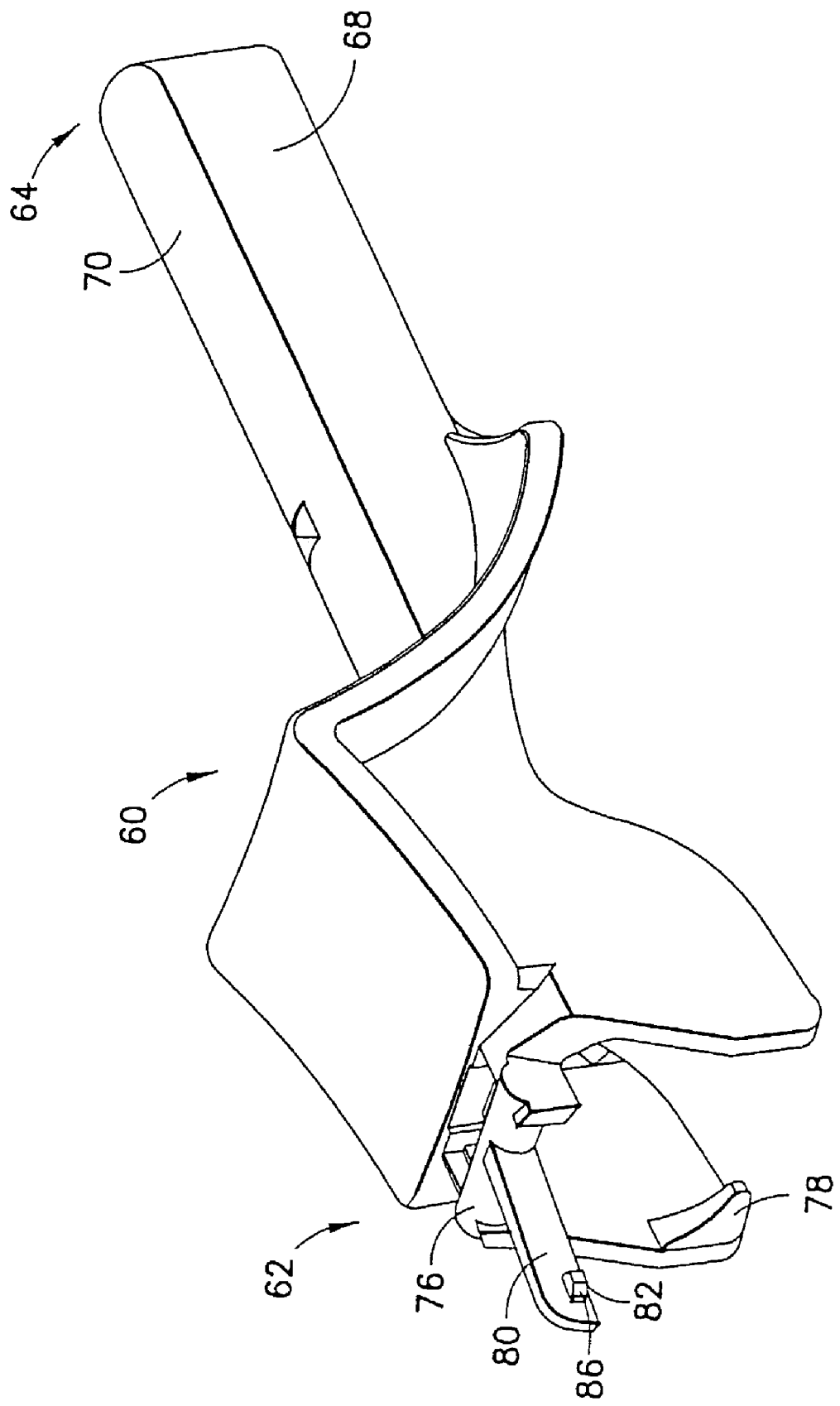
FIG. 5 is an enlarged perspective view of the shield.
Figure 6:
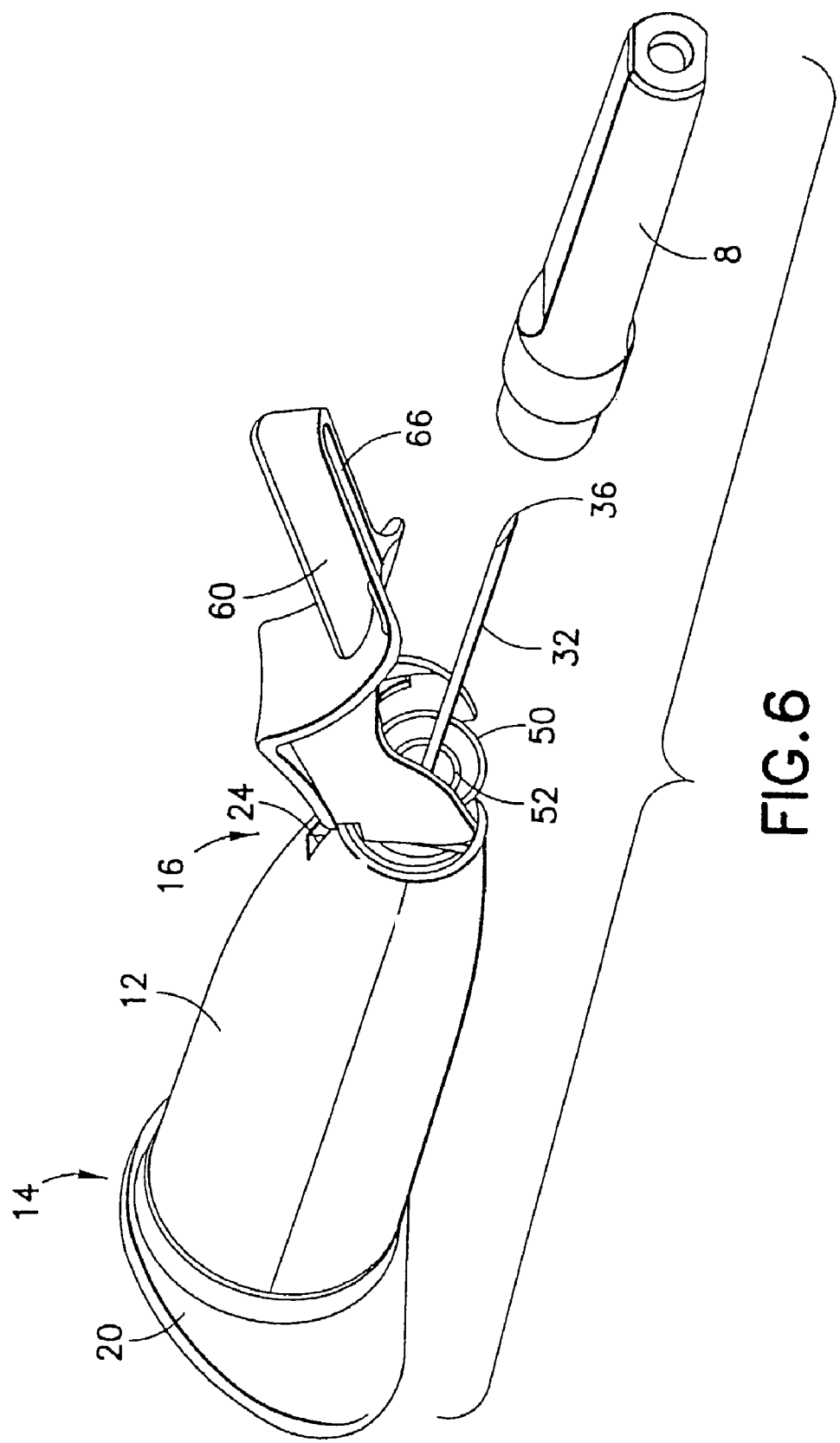
FIG. 6 is a perspective view of the blood collection assembly of FIG. 1 with the packaging cover removed, and with the shield in a retracted position.

Means for trapping needle cannula 32 in slot 66 may be provided in the form of a cannula lock including an arm 74 that may extend downward from top section 70 as shown in FIG. 4, to secure the shield 60 over the needle cannula 32 after use. Arm 74 is deflectable by needle cannula 32 when the needle cannula 32 enters slot 66. Once needle cannula 32 passes the end of arm 74, arm 74 moves back to its original position, whereby needle cannula 32 is permanently trapped in slot 66 by arm 74.

As an additional locking mechanism, hub 40 may include locking dents or protrusions 56 for engagement with barb dents 78 located at the proximal end 62 of shield 60. Barb dents 78 cooperate with locking dents 56 on hub 40 to secure shield 60 in its final locked or shielded position. Also, the interior surface of shield 60 within slot 66 may be designed in a manner for urging needle cannula 32 toward the center of slot 66 as shield 60 is being pivoted into the closed position.

Shield 60 is further provided with locking structure for releasably maintaining shield 60 in the retracted position, such as a retaining member in the form of retaining arm 80. Retaining arm 80 extends from proximal end 62 of shield 60 in a proximal direction. Desirably, retaining arm 80 extends from hanger bar 76. Needle holder 12 may include a notch 24 at the top wall of distal end 16 thereof for accommodating retaining arm 80.

Retaining arm 80 and hub 40 include interengaging structure to provide for releasable engagement therebetween. For example, retaining arm 80 may include a locking lug 82 extending from retaining arm 80, desirably in a direction transverse to the axis of needle assembly 30. Hub 40 may include a corresponding locking recess 84 for accommodating locking lug 82 of retaining arm 80 when shield 60 is in the retracted position. Retaining arm 80 is flexible and deflectable in a transverse direction, and is in a biased state when deflected tranversely. As such, when retaining arm 80 is deflected such that locking lug 82 is released from interference engagement within locking recess 84, retaining arm 80 is biased toward a return movement within locking recess 84. It is contemplated that any locking structure can be used to lock and releasably maintain shield 60 in the retracted position. For example, the arrangement of the locking lug and the locking recess can be reversed, such that the retaining member includes a locking recess and the hub includes a locking lug for engagement therewith.

An actuator 90 is provided for releasing the locking structure to permit pivoting of the shield. Actuator 90 is a generally elongate structure extending between a proximal end 92 and a distal end 94. Actuator 90 is slidably engaged with or mounted on hub 40, such as within guide channel 58, and extends through distal end 16 and into the interior of needle holder 12, desirably at a location adjacent proximal end 34 of needle cannula 32. Actuator 90 is provided for engagement with retaining arm 80 to release it from locking engagement.

As such, retaining arm 80 includes a lug cam surface 86 on locking lug 82 at the proximal end of retaining arm 80, and actuator 90 includes a corresponding cam surface 96 at its distal end 94. As will be discussed in more detail herein, axial movement of actuator 90 within the guide channel 58 of hub 40 causes cam surface 96 to contact lug cam surface 86 on retaining arm 80, thereby deflecting retaining arm 80 in a transverse direction and disengaging locking lug 82 from interference engagement within locking recess 84 of hub 40.

A biasing member, such as spring 100, is further provided. Spring 100 includes stored energy when shield 60 is in the retracted state, and provides a biasing force for biasing shield 60 about its pivot axis toward the shielded position encompassing needle cannula 32. Spring 100 may be any biasing member capable of biasing shield 60 toward the shielded position, such as a wound torsion spring or coil spring, a leaf spring, and the like. Desirably, spring 100 is coiled or wound about the pivoting hinge established through the engagement of hook member 54 and hanger bar 76. Alternatively, it is further contemplated that a biasing member may be provided between retaining arm 80 and hub 40, such as a spring capable of forcing retaining arm 80 away from hub 40, thereby causing pivoting of shield 60.

Blood collection assembly 10 may be packaged with packaging cover 8 disposed over distal end 36 of needle cannula 32. Optionally, the proximal end 14 of the needle holder 12 can be covered with a paper-like membrane that is thermally or adhesively sealed onto the proximal end 14 of needle holder 12. Examples of materials used for a paper-like membrane are Tyvek® manufactured by DuPont and examples of materials to be used for a thermoformed blister package include glycol modified polyethylene terephthalate (PETG), polyethylene terephthalate (PET), high-density polyethylene, polypropylene, polycarbonate, nylon, and K-resin. The assembly may alternatively be packaged and sealed in a blister package having a thermoformed blister and top web. The top web is comprised of a material that may be permeable to gas such as ethylene oxide gas. In the configuration with a paper-like membrane covering the open proximal end 14 of needle holder 12, a thermoformed blister and top web would not be required, and the entire assembly can be sterilized by ethylene oxide gas or cobalt 60 irradiation. Alternatively, needle holder 12 and needle assembly 30 may be separate components packaged separately. For example, needle assembly 30 may be provided in a hardpack type assembly with a packaging cover 8 disposed over distal end 36 of needle cannula 32, and with a second packaging cover (not shown) disposed over proximal end 34 of needle cannula 32 and removably mated with hub 40. In such an arrangement, the packaging covers can be removed prior to use, and needle assembly 30 can be mated with needle holder 12, for example through threaded engagement therebetween.

In use, blood collection assembly 10 may be provided as shown in FIG. 1. Alternatively, needle holder 12 and needle assembly 30 may be provided as separate components which are attached to each other, such that proximal end 34 of needle cannula 32 and actuator 90 extends within needle holder 12. Any membrane covering the open proximal end 14 of needle holder 12 is removed, and the packaging cover 8 is removed by the user, thereby exposing distal end 36 of needle cannula 32. Blood collection assembly 10 is then ready in the sampling state, with shield 60 in a retracted position exposing needle cannula 32 for use, as shown in FIGS. 7-8. The medical practitioner then sterilizes the intended area of puncture on the patient's body, and a venipuncture procedure can then be conducted whereby the puncture tip of distal end 36 of the needle cannula 32 is inserted through the skin and into a vein of a patient.

Prior to insertion of a blood collection tube 26 into needle holder 12 for sampling, spring 100 is exerting a biasing force against shield 60 toward the shielded position. Locking lug 82 of retaining arm 80 is in a resting state in interference engagement within locking recess 84 of hub 40. Since retaining arm 80 is an extension of shield 60, the interference engagement between locking lug 82 and locking recess 84 acts as a lock for maintaining shield 60 in the retracted position against the spring bias. It is noted that the biasing force exerted on shield 60 through spring 100 is sufficient to cause shield 60 to be pivoted to the shielded position, but is less than the force required to maintain locking lug 82 in interference engagement with locking recess 84. As such, locking lug 82 effectively locks shield 60 in the retracted position against the biasing force of spring 100. Also, at this point actuator 90 is in a retracted position as shown in FIGS. 9-13. In such a position, actuator 90 extends within guide channel 58 of hub 40, but does not engage retaining arm 80.

Initial activation of shield 60 is achieved automatically and passively by insertion of a blood collection tube 26 into proximal end 14 of needle holder 12. Sufficient insertion of blood collection tube 26 into needle holder 12 will cause proximal end 34 of needle cannula 32 to displace and pierce sleeve 48, as well as to pierce through the elastomeric septum 28 that extends across the open end of blood collection tube 26, as shown in FIG. 14. Distal movement of blood collection tube 26 into needle holder 12 also will cause blood collection tube 26 to engage proximal end 92 of actuator 90, thereby causing actuator 90 to slide axially and distally through guide channel 58 of hub 40. This distal movement of actuator 90 will cause cam surface 96 at distal end 94 of actuator 90 to engage lug cam surface 86 of retaining arm 80 with sufficient force to transversely deflect or pivot retaining arm 80 a sufficient distance to disengage locking lug 82 from within locking recess 84 of hub 40, thereby releasing the interference engagement established by the corresponding surfaces of locking lug 82 and locking recess 84.

Figure 15:
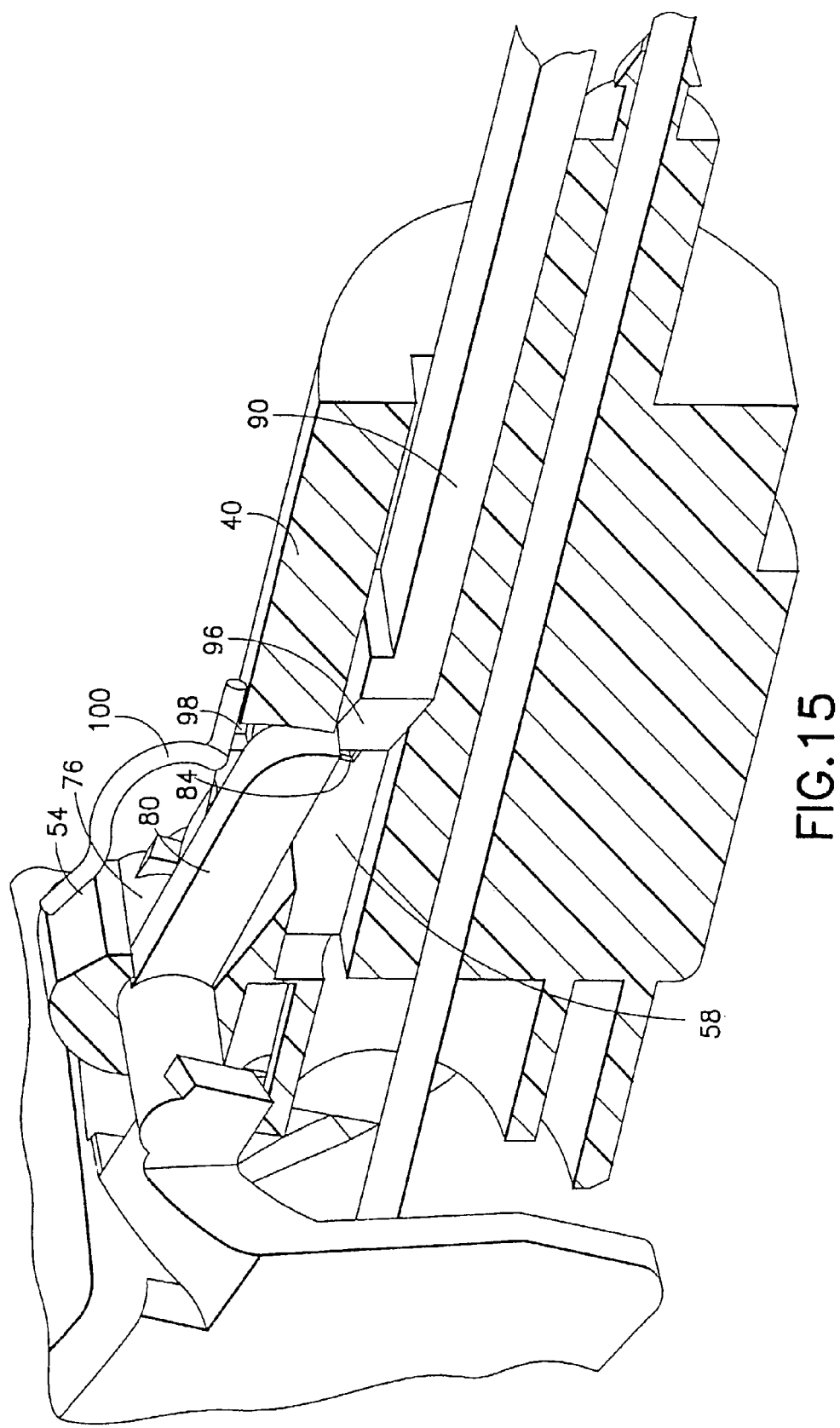
FIG. 15 is an enlarged view showing the engagement between the actuator and the retaining arm during pivotal movement of the shield toward the shielded position in use.
Figure 16:
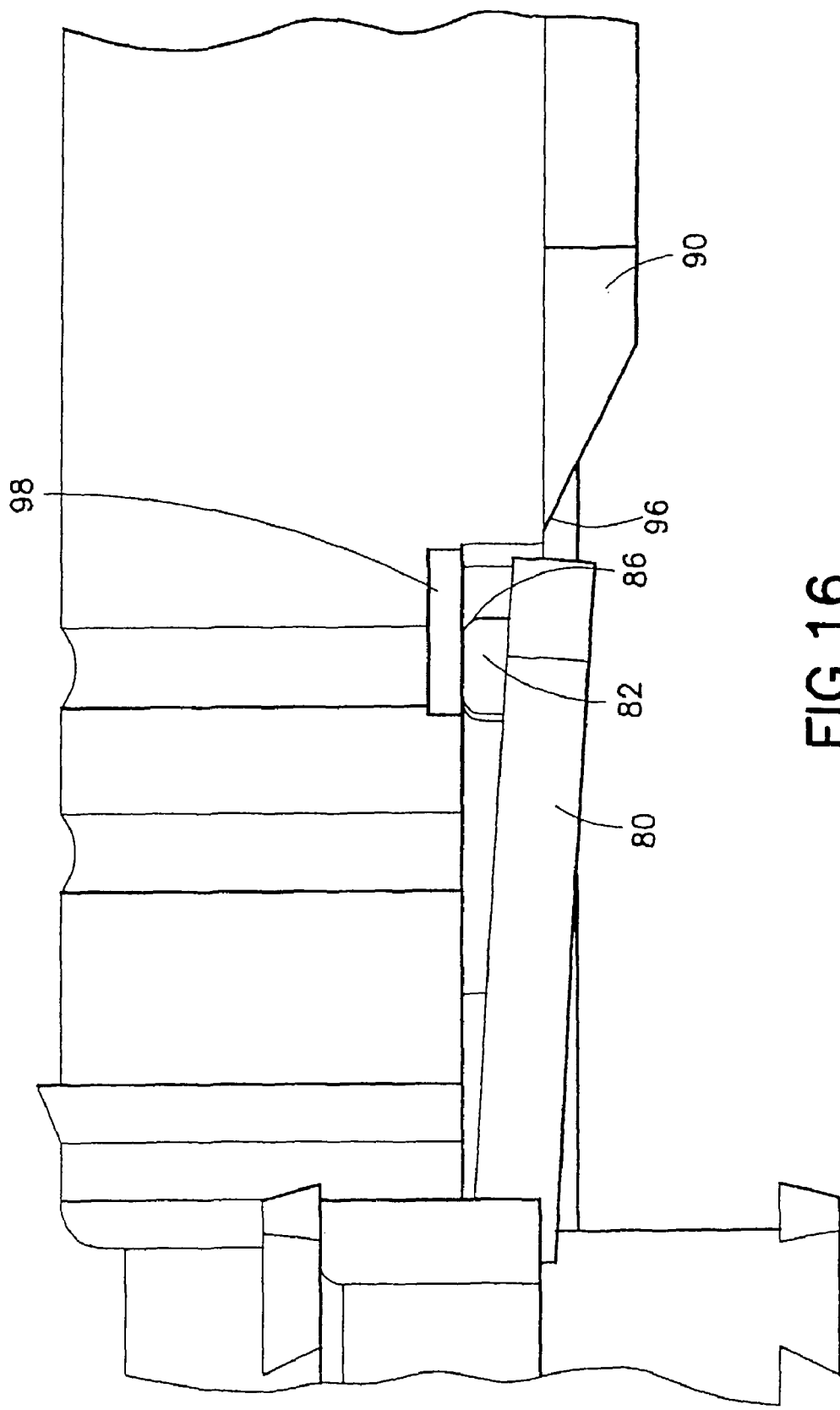
FIG. 16 is an enlarged top elevation view showing the engagement between the actuator and the retaining arm during pivotal movement of the shield toward the shielded position.
Figure 17:
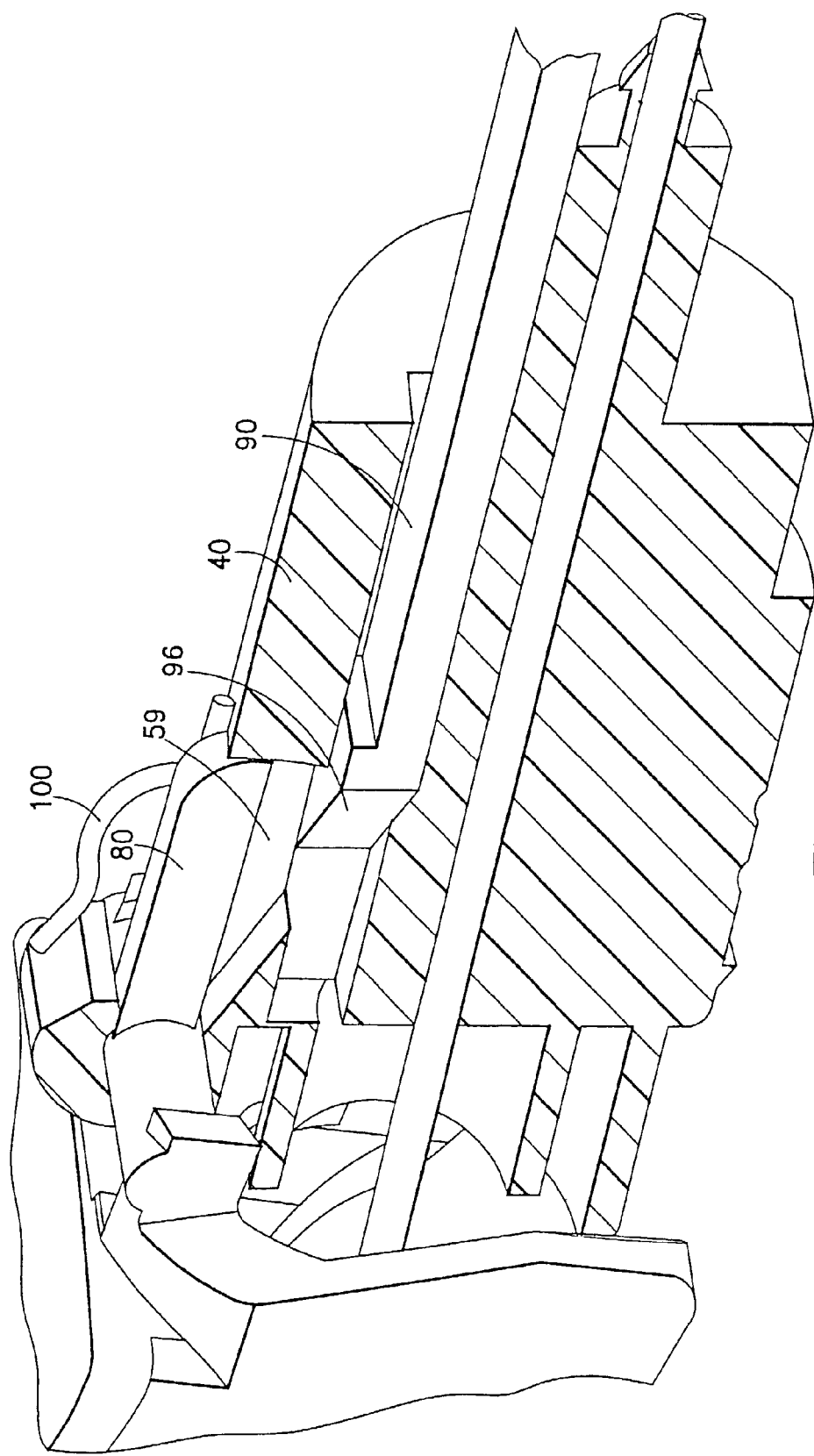
FIG. 17 is an enlarged view showing the actuator and the retaining arm with the shield locked in the fully shielded position.
Figure 18:
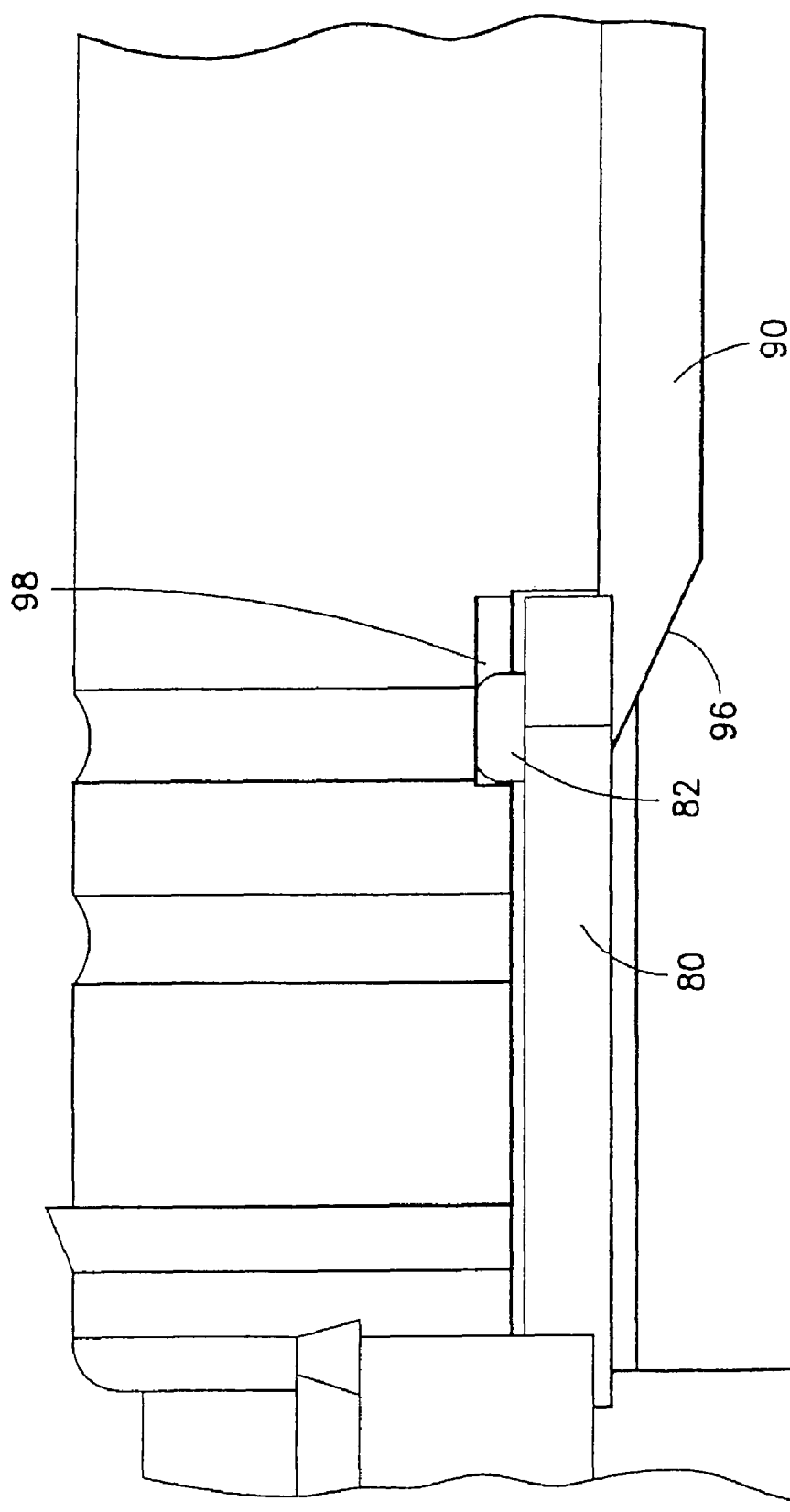
FIG. 18 is an enlarged top elevation view showing the actuator and the retaining arm with the shield locked in the fully shielded position.

Disengagement of locking lug 82 from latch recess 84 releases the lock of shield 60, thereby permitting shield 60 to be propelled pivotably about the pivot axis established through hook member 54 and hanger bar 76 under the action of spring 100. During such pivotal movement, retaining arm 80 is also pivoted within a forward opening area 59 of guide channel 58. Also, the transverse deflection of retaining arm 80 creates a biasing force on retaining arm 80, forcing locking lug 82 against the wall surface of the opening area 59 within guide channel 58, as shown in FIGS. 15-16. Locking lug 82 will be guided in the forward opening 59 of guide channel 58 as shield 60 is pivoted toward the shielding position. Since distal end 36 of needle cannula 32 extends through the patient's skin, shield 60 will pivot to a point where forward end wall 72 contacts the patient's skin, as shown in FIG. 14. The force of spring 60 should not be sufficient so as to propel shield 60 in a pivoting nature against the skin of the patient with sufficient force to startle or alert the patient or to traumatize the tissue or move the needle cannula within the patient. To this end, spring dampening agents and the like may be used.

Upon completion of the sampling procedure, blood collection tube 26 is withdrawn from needle holder 12, and distal end 36 of needle cannula 32 is withdrawn from the patient. This causes shield 60 to automatically pivot to the fully shielded position under the bias of spring 100, since locking lug 82 is within the forward opening area 59 of guide channel 58 and is free from engagement with any locking recess.

Upon complete pivoting of shield 60 to the fully shielded state, shield 60 encompasses needle cannula 32. Retaining arm 80 pivots within the forward opening of guide channel 58 with the pivoting of shield 60. Upon full pivotal movement, locking lug 82 engages within a second locking recess 98 at the top surface of the forward opening of guide channel 58. Since retaining arm 80 is deflected and biased against the wall surface of the opening area 59 during pivotal movement, it is forced within second locking recess 98 during pivotal movement, thus providing an interference engagement between locking lug 82 and second recess 98 for preventing a return movement of retaining arm 80 within the guide channel. As such, shield 60 is locked in the shielded position encompassing distal end 36 of needle cannula 32.

During pivotal rotation of shield 60 to the shielded position, barb dents 78 deflect over and are held by locking dents 56 of hub 40. The interengagement between barb dents 78 and locking dents 56 provides a further locking structure for locking engagement between shield 60 and hub 40, thereby locking shield 60 in the shielded position and preventing pivotal rotation of shield 60 to the open or retracted position. In embodiments including a needle cannula locking mechanism such as arm 74, the needle cannula 32 snaps past arm 74 and is trapped when needle cannula 32 is contained within shield 60 as shield 60 is pivoted into the closed or shielded position. Alternatively or in addition, a gel material may be located in the shield near arm 74 so that when needle cannula 32 snaps past arm 74, it will come to rest within the gel material. The gel material will contain any residual fluid that may be on needle cannula 32.

As such, blood collection assembly 10 is in a final, non-retractable shielded position whereby needle cannula 32 is trapped in longitudinal opening 66, and can be appropriately discarded.

The present invention provides an effective device and method for passively shielding a needle cannula through a standard sequence of operation of a medical procedure, specifically a blood collection procedure. As such, no additional movement or separate action is required by the practitioner in order to shield the used needle. In addition, the shielding of the needle cannula can be automatically initiated during the procedure while the needle cannula is maintained within the patient, with the final shielding occurring upon removal of the needle cannula from the patient. Accordingly, exposure to the used needle is minimized.

While the present invention has been described in terms of specific embodiments for use in connection with a blood collection system, it is further contemplated that the assembly and the components thereof can be used with other medical procedures known in the art.

The invention claimed is:

1. A shieldable needle assembly comprising:
a needle cannula having a proximal end and a distal end;
a hub mounted to the needle cannula at a location spaced from the distal end;
a shield having a proximal end and a distal end in pivotal engagement with the needle cannula and moveable about a pivot axis between a retracted position in which the distal end of the shield is pivotally spaced from the needle cannula, and a shielded position in which the distal end of the shield encompasses the distal end of the needle cannula;
a biasing member having stored energy when the shield is in the retracted position capable of biasing the pivoting shield towards the shielded position;
a lock for releasably maintaining the pivoting shield in the retracted position; and
a linearly movable actuator for releasing the lock, the actuator adapted to passively activate upon contact with a container during a standard sequence of operation of a medical procedure, wherein the actuator is configured to convert the linear movement thereof to pivotal movement of the shield to the shielded position.

2. The assembly of claim 1 wherein the hub includes a locking recess and the shield includes a retaining arm including a locking lug engageable with the locking recess.

3. The assembly of claim 2 further including a second locking recess in the hub wherein the retaining arm is engageable with the second locking recess to secure the pivoting shield in the shielded position encompassing the needle cannula.

4. The assembly of claim 1, wherein the actuator is activated to release the lock by pressure applied during a standard sequence of operation of a medical procedure, and wherein the pivoting shield will move toward the shielded position upon activation of the actuator to release the lock.

5. The assembly of claim 1, wherein the shield includes a retaining arm for engagement with the hub to form the lock.

6. The assembly of claim 5, wherein one of the hub and the retaining arm includes a locking recess and the other of the hub and the retaining arm includes a locking lug, wherein the locking lug is engageable with the locking recess to form the lock, and wherein the actuating arm disengages the locking lug from the locking recess to release the lock.

7. The assembly of claim 1, wherein the biasing member is a spring, wherein the spring has a spring force less than the force required to release the lock.

8. The assembly of claim 1, wherein the hub is adapted for mating with a needle holder, and wherein the actuator is activated by pressure applied through insertion of a blood collection tube within the needle holder.

9. A shieldable needle assembly comprising:
a needle cannula having a proximal end and a distal end;
a hub mounted to the needle cannula at a location spaced from the distal end;
a shield pivotally mounted to the hub and in pivotal engagement with respect to the needle cannula wherein the shield includes a lock for releasably maintaining the shield in a retracted position with the shield pivotally spaced from the distal end of the needle cannula;
a biasing member having stored energy when the shield is in the retracted position capable of biasing the pivoting shield about a pivot axis located at the hub towards the shielded position wherein the pivot axis is fixed with respect to the shield and the hub; and
an actuator for releasing the lock,
wherein the actuator is activated to release the lock by indirect pressure applied proximal to the hub during a standard sequence of operation of a medical procedure and wherein the pivoting shield will move toward the shielded position upon activation of the actuator to release the lock.

10. A shieldable needle assembly comprising:
a needle cannula having a proximal end and a distal end;
a hub mounted to the needle cannula at a location spaced from the distal end;
a shield pivotally mounted to the hub and in pivotal engagement with respect to the needle cannula, wherein the shield includes a lock for releasably maintaining the shield in a retracted position with the shield pivotally spaced from the distal end of the needle cannula;

a biasing member having stored energy when the shield is in the retracted position capable of biasing the pivoting shield about a pivot axis located at the hub towards the shielded position wherein the pivot axis is fixed with respect to the shield and the hub; and an actuator advanceable in a linear direction from a proximal to a distal orientation for releasing the lock, wherein the actuator is activated to release the lock by pressure applied during a standard sequence of operation of a medical procedure and wherein the pivoting shield will move toward the shielded position upon activation of the actuator to release the lock.

11. A blood collection assembly comprising:
a needle cannula;
a hub mounted on the needle cannula;
a spring biased pivoting shield pivotably mounted to the hub and moveable about a pivot axis between a retracted position and a shielded position encompassing a distal end of the needle cannula;
a needle holder having a first end mated with the hub and a second end adapted for receiving a blood collection container; and
a retaining member attached to the pivoting shield and releasably engageable with the hub,
wherein the retaining member maintains the pivoting shield in the retracted position against the spring bias when engaged with the hub, and wherein insertion of a blood collection container into the needle holder and into contact with the actuator causes a passive release of the retaining member from engagement with the hub, wherein the retaining member is configured for converting the application of a linear force within the needle holder to pivotal movement of the shield thereby causing the pivoting shield to move toward the shielded position due to the spring bias.

12. The assembly of claim 11 wherein the retaining member includes at least one retaining arm extending from the pivoting shield for engagement with the hub.

13. The assembly of claim 12 wherein the retaining arm includes a locking lug and the hub includes a locking recess, the locking lug and locking recess in interference engagement to maintain the pivoting shield in the retracted position against the spring bias.

14. The assembly of claim 13, further comprising an actuator extending within the needle holder, the actuator capable of releasing the locking lug from interference engagement with the locking recess upon insertion of a blood collection container into the needle holder.

15. The assembly of claim 11 wherein the spring biased pivoting shield includes a torsion spring biasing the pivoting shield toward the shielded position, wherein the biasing force of the spring is less than the force required to cause the retaining member to release from engagement with the hub.

16. A blood collection assembly comprising:
a needle cannula;
a hub mounted on the needle cannula;
a pivoting shield mounted on the hub and pivotable between a retracted position and a shielded position encompassing a distal end of the needle cannula;
a spring mounted on the hub biasing the pivoting shield towards the shielded position;
a lock on the hub maintaining the pivoting shield in the retracted position against the bias of the spring;
a needle holder having a first end mated with the hub and a second end adapted for receiving a blood collection tube; and a linearly movable actuator in moveable engagement with the hub for releasing the lock, wherein insertion of a blood collection tube in the needle holder and into contact with the actuator passively activates the linear movement of the actuator to cause release of the lock, thereby releasing the bias of the spring and allowing the pivoting shield to move toward the shielded position.

17. The assembly of claim 16 wherein the actuator includes an actuating arm extending within the needle holder and capable of engaging with a blood collection tube within the needle holder.

18. The assembly of claim 17 wherein the pivoting shield includes a retaining arm extending therefrom, and wherein one of the hub and the retaining arm includes a locking recess and the other of the hub and the retaining arm includes a locking lug, wherein the locking lug is engageable with the locking recess to form the lock, and wherein the actuating arm disengages the locking lug from the locking recess to release the lock.

19. The assembly of claim 18 wherein the actuating arm disengages the locking lug from the locking recess through an axial movement of the actuating arm.

20. The assembly of claim 19 wherein the actuating arm and the locking lug include corresponding camming surfaces for causing the locking lug to move transversely with respect to the actuating arm upon axial movement of the actuating arm.

21. A method of shielding a needle comprising:
providing a needle holder adapted for receiving a blood collection tube;
providing a needle assembly mated with the needle holder, the needle assembly comprising a hub mounted to a needle cannula with a spring biased pivoting shield mounted on the hub, the pivoting shield including a retaining member engaging the hub to releasably maintain the pivoting shield against the spring bias to prevent the pivoting shield from moving to a shielded position encompassing the needle cannula; and
inserting a blood collection tube into the needle holder into contact with the retaining member wherein initial contact therewith causes the retaining member to disengage from the hub, thereby causing the pivoting shield to be biased toward the shielded position.

22. The method of claim 21 further comprising an actuator extending between the needle holder and the needle assembly, wherein inserting a blood collection tube into the needle holder causes axial movement of the actuator which causes the retaining member to disengage from the hub, thereby causing the pivoting shield to be biased toward the shielded position.

23. The method of claim 22 wherein one of the hub and the retaining member includes a locking recess and the other of the hub and the retaining member includes a locking lug, wherein the locking lug is engageable with the locking recess to releasably maintain the pivoting shield against the spring bias to prevent the pivoting shield from moving to a shielded position encompassing the needle cannula.

24. The method of claim 23 wherein insertion of a blood collection tube within the needle holder causes the actuator to disengage the locking lug from the locking recess.

25. The method of claim 21 further including the step of locking the pivoting shield in the shielded position.

* * * * *